(12) United States Patent
Strehlow

(10) Patent No.: US 6,887,853 B2
(45) Date of Patent: May 3, 2005

(54) USE OF GELDANAMYCIN AND RELATED COMPOUNDS FOR TREATMENT OF FIBROGENIC DISORDERS

(75) Inventor: David Strehlow, Wayland, MA (US)

(73) Assignee: The Trustees of Boston University, Boston, MA (US)

( * ) Notice: Subject to any disclaimer, the term of this patent is extended or adjusted under 35 U.S.C. 154(b) by 0 days.

(21) Appl. No.: 10/312,287

(22) PCT Filed: Jun. 28, 2001

(86) PCT No.: PCT/US01/20578

§ 371 (c)(1),
(2), (4) Date: Dec. 20, 2002

(87) PCT Pub. No.: WO02/02123

PCT Pub. Date: Jan. 10, 2002

(65) Prior Publication Data

US 2004/0082498 A1 Apr. 29, 2004

Related U.S. Application Data

(60) Provisional application No. 60/214,950, filed on Jun. 29, 2000.

(51) Int. Cl.$^7$ ............................ A61K 31/70; A61K 31/33

(52) U.S. Cl. .......................................... 514/26; 514/183

(58) Field of Search .................................... 514/26, 183

(56) References Cited

U.S. PATENT DOCUMENTS

| | | | |
|---|---|---|---|
| 4,261,989 A | | 4/1981 | Sasaki et al. ................ 424/244 |
| 4,673,637 A | | 6/1987 | Hyman ........................ 435/34 |
| 5,449,678 A | * | 9/1995 | Pines et al. ............. 514/266.22 |
| 6,015,659 A | * | 1/2000 | Welch et al. ................ 435/1.2 |
| 6,174,875 B1 | * | 1/2001 | DeFranco et al. .......... 514/183 |

* cited by examiner

Primary Examiner—Raymond J. Henley, III
(74) Attorney, Agent, or Firm—Weingarten, Schurgin, Gagnebin & Lebovici LLP

(57) ABSTRACT

A method for prophylaxis or treatment of a mammal, particularly human, at risk for a fibrogenic disorder is disclosed. The compositions and methods of the invention are directed both to treatments for existing fibrogenic disorders and prevention thereof. Such disorders include, but are not limited to, connective tissue diseases, such as scleroderma (or systemic sclerosis), polymyositis, systemic lupus erythematosis and rheumatoid arthristis, and other fibrotic disorders, including liver cirrhosis, keloid formation, interstitial nephritis and pulmonary fibrosis. A therapeutic composition according to the invention includes, as a therapeutic agent, an inhibitor of a collagen promoter in a pharmaceutically acceptable inert carrier vehicle, preferably for local, and particularly topical, application. Exemplary inhibitors include those that interfere with heat shock protein 90 (Hsp 90) chaperone function, e.g., the specific inhibitor geldanamycin or other known Hsp90 inhibitors such as macbecin I and II, herbimycin, radcicol and novobiocin.

11 Claims, 11 Drawing Sheets

Expressed Gene Array Fingerprint of
Scleroderma Lesional Dermal Fibroblast mRNA
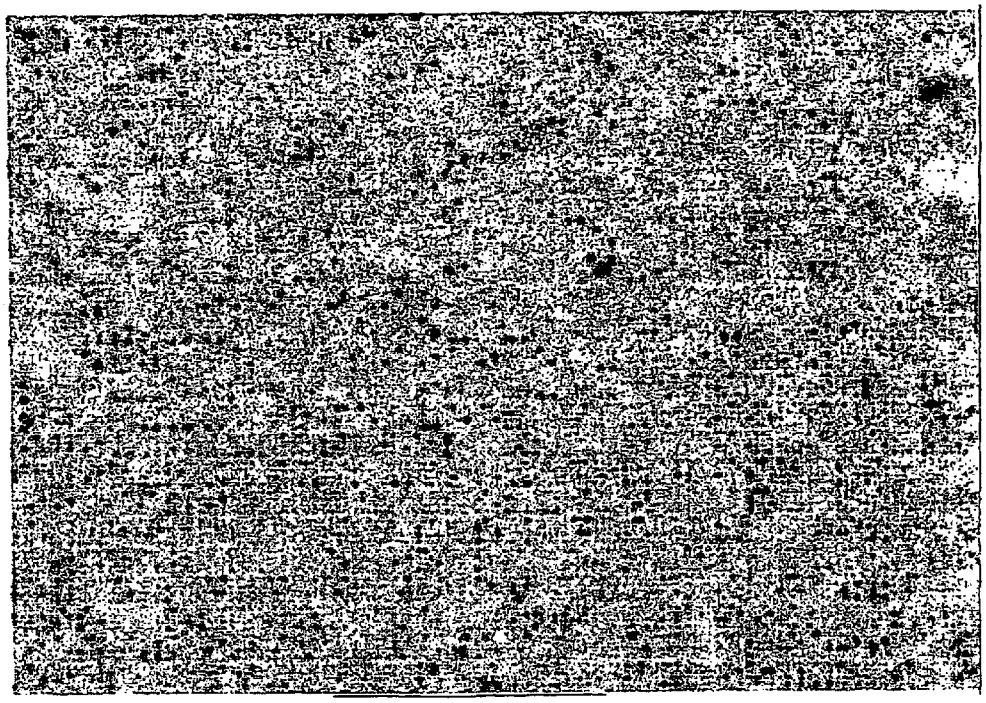
FIG. 1A
Microarray Comparison of Three Healthy
and Three Scleroderma Lesional Fibroblast Lines
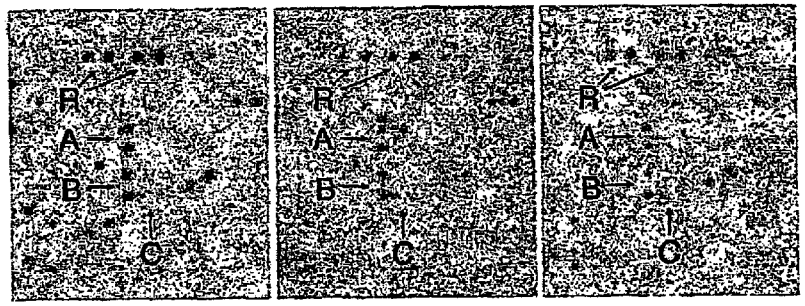
FIG. 1B
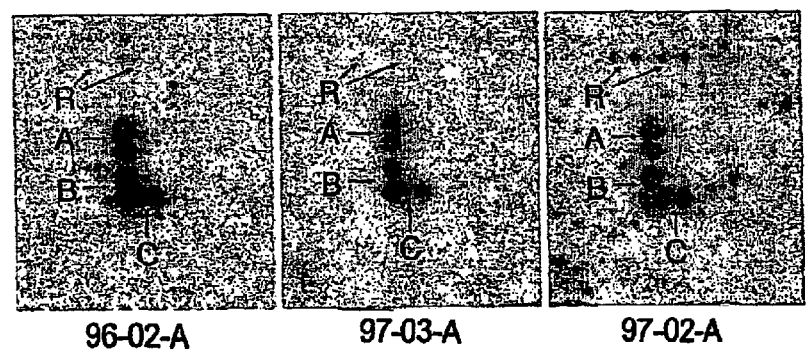

USE OF GELDANAMYCIN AND RELATED COMPOUNDS FOR TREATMENT OF FIBROGENIC DISORDERS

CROSS REFERENCE TO RELATED APPLICATIONS

This application is a 371 of PCT/US01/20578, filed Jun. 28, 2001, which claims the priority of U.S. Provisional Application No. 60/214,950 filed Jun. 29, 2000 entitled, A USE FOR GELDANAMYCIN AND DERIVATIVES AS INHIBITORS OF TGF-β SIGNALING AND EXTRACELLULAR MATRIX SYNTHESIS, the whole of which is hereby incorporated by reference herein.

STATEMENT REGARDING FEDERALLY SPONSORED RESEARCH OR DEVELOPMENT

Part of the work leading to this invention was carried out with United States Government support provided by the National Institutes of Health under Grant No. RO1 AR-47196. Therefore, the U.S. Government has certain rights in this invention.

BACKGROUND OF THE INVENTION

Systemic sclerosis, or scleroderma (SSc), is characterized by three features: increased extracellular matrix accumulation in the skin and organs, vascular injury and tissue ischemia, and immune cell activation and autoantibody production. The disease is one of a class of connective tissue diseases including polymyositis, systemic lupus erythematosis, and rheumatoid arthritis, which all share some common immunological features and are sometimes found within families.

Several studies show specific HLA patterns associated with autoantibody production (1). However, family studies in the general population show only a weak genetic predisposition to scleroderma. One exception to this has been described for Choctaw Native Americans (2). This group has a high prevalence of scleroderma (469/100,000) and an HLA DR2 haplotype that is strongly associated with the disease. Preliminary mapping suggests that there may be a defect in the fibrillin gene (3), which is also thought to be defective in one of the few animal models for scleroderma, that of the mutant mouse line, Tsk-1 (4,5).

While the disease may have an underlying genetic basis in some cases, in the general population it is a complex trait that involves genetic risk factors and, in some cases, may also involve environmental toxins (6,7). New methods of treating scleroderma and related conditions would be very useful.

BRIEF SUMMARY OF THE INVENTION

The present invention encompasses both prophylactic and therapeutic treatments for a mammal, preferably a human, at risk for a fibrogenic disorder. In particular, the compositions and methods of the present invention are directed both to treatments for existing fibrogenic disorders and prevention thereof. Such disorders include, but are not limited to, connective tissue diseases, such as scleroderma (or systemic sclerosis), polymyositis, systemic lupus erythematosis and rheumatoid arthritis, and other fibrotic disorders, including liver cirrhosis, keloid formation, interstitial nephritis and pulmonary fibrosis.

A therapeutic composition according to the invention includes, as a therapeutic agent, an inhibitor of collagen promoter activity in a pharmaceutically acceptable inert carrier vehicle, preferably for local, and particularly topical, application. Exemplary inhibitors include those that interfere with heat shock protein 90 (Hsp90) chaperone function, e.g., the specific inhibitor geldanamycin or other known Hsp90 inhibitors such as macbecin I and II, herbimycin, radcicol and novobiocin.

In another embodiment, the present invention is directed to an article of manufacture comprising a packaging material and a therapeutic composition of the present invention contained within the packaging material. The therapeutic composition is therapeutically effective for prophylaxis or treatment of fibrogenic disorders. The packaging material also comprises a label with instructions for use, which indicate that the therapeutic composition can be used for prophylaxis or treatment of fibrogenic disorders.

BRIEF DESCRIPTION OF THE DRAWINGS

Other features and advantages of the invention will be apparent from the following description of the preferred embodiments thereof and from the claims, taken in conjunction with the accompanying drawings, in which:

FIG. 1A shows hybridization of labeled mRNA from cultured scleroderma fibroblasts to a large array of expressed sequence tags. FIG. 1B shows hybridization of mRNA from 3 healthy fibroblast lines (N-96-05, N-96-02, N-92-04) and from 3 scleroderma lines (96-02-A, 97-03-A, 97-02-A) to identical large array filters. Each clone on the filters is represented by two spots. R points to two reference clones whose intensity is unchanged between the healthy and scleroderma cells when compared to spots in other regions of the filter. A, B and C are comparable to R in the healthy lines. However, A, B and C are several-fold more intense than R in the scleroderma lines;

DETAILED DESCRIPTION OF THE INVENTION

Figure 2:
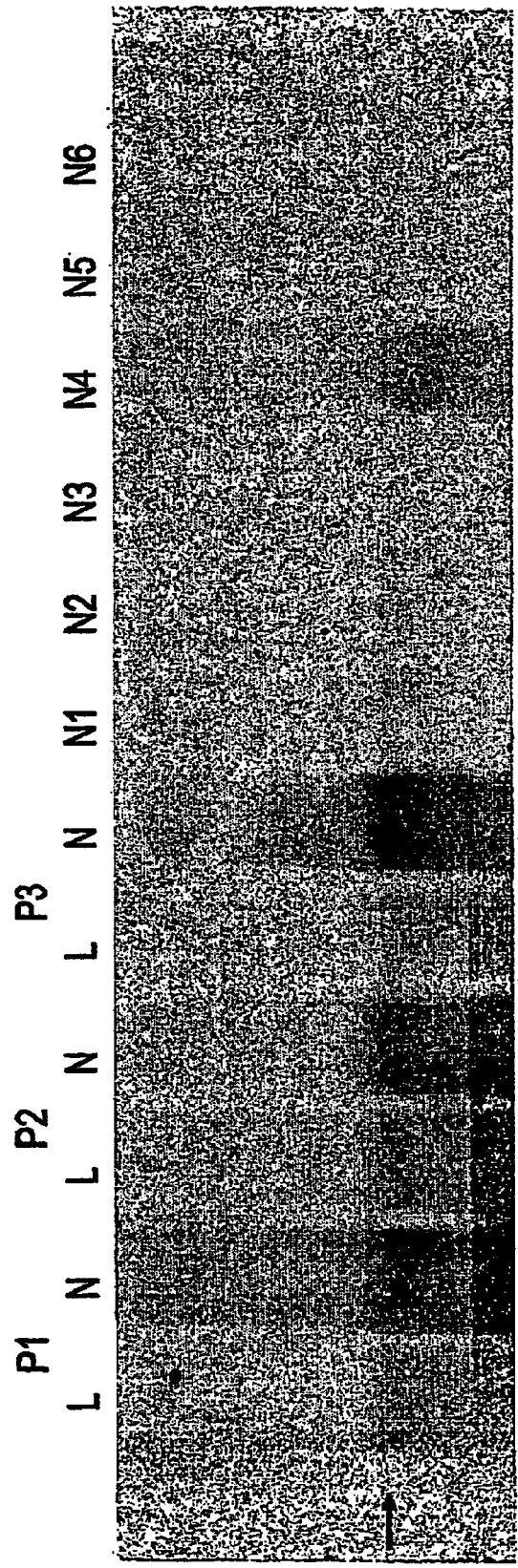
FIG. 2 shows northern analysis using the insert from clone A of FIG. 1B as a probe. Total RNA from lesional (L) or nonlesional (N) fibroblast lines from three scleroderma patients (P1–P3) or from 6 healthy fibroblast lines (N1–N6) was analyzed. The arrow shows the size of the Hsp90 message.

Fibroblasts grown from dermal scleroderma biopsies have been shown to maintain a fibrogenic phenotype for several passages in culture (8,9). Since these cells maintain a disease-like phenotype, they are a useful model system for scleroderma skin and, therefore, are appropriate candidates for analysis of differential gene expression.

In the work leading to the- invention, microarrays were utilized to characterize the gene expression pattern in the scleroderma fibroblast model system. The goal of such experiments was to characterize individual genes from the scleroderma expression fingerprint in order to identify those which might lie in a pathway of expressed genes responsible for the scleroderma phenotype—excessive matrix deposition. Initial differential display studies were expanded using densely printed microarrays on nylon filter membranes.

In the current work, filter membranes containing large arrays of expressed sequence tags (ESTs) were probed with radioactively labeled mRNA isolated from independent scleroderma and healthy dermal fibroblast lines. These filters are commercially available and contain over 18,000 different clones each spotted in duplicate. Four different scleroderma lesional, non-lesional and healthy lines—12 in all—were utilized as sources of RNA. Several genes were consistently overexpressed or underexpressed in the scleroderma lines compared to the healthy controls. Among those that were overexpressed was the gene for heat shock protein 90 alpha (Hsp90). Because of the 97% homology between the genes for Hsp90α and Hsp90β, these genes were chosen for further study.

Hsp90 is a cytosolic protein conserved in species as diverse as bacteria and primates. One function of Hsp90 is to protect proteins from aggregating during thermal stress (12). Another important function is as a hormone receptor chaperone. Genetic studies in yeast (13,14) and molecular studies in higher cells (15) show that Hsp90 is required for hormone receptors to bind hormone. Without Hsp90, or in the presence of the specific inhibitor of Hsp90, the benzamycin ansiquinone geldanamycin (16), hormone receptor signal response fails.

The ATP binding site on Hsp90 (17) is required for normal chaperone function. Geldanamycin binds to the ATP binding site in Hsp90 (18) and thus may block hormone receptor function by starving Hsp90 of ATP. Many different hormone receptors can bind Hsp90, including those for estrogen (19), progesterone (20), and aryl hydrocarbons (21) (including dioxin (22)). Hsp90 also exhibits chaperone activity for other signal transduction molecules, including casein kinase II (23), pp60$^{v-src}$ (24), eIF2α kinase (25). Studies using null mutations of Hsp90 in *Drosophila* (Hsp83) show that it modulates Raf signaling (26) and signaling by the sevenless receptor tyrosine kinase (27).

Signal transduction by TGF-β may play an important role in the scleroderma phenotype. TGF-β is a potent fibrogenic cytokine that stimulates the transcription and synthesis of multiple matrix-encoding genes (28). The TGF-β family is thought to transduce its signal through a family of cytosolic proteins known as Smads (29). TGF-β binds to the type II TGF-β receptor, which propagates the signal through the type I receptor to Smad. The family of human Smad proteins includes at least 9 members (30). Smad 2 or Smad 3 proteins are transiently associated with the type I receptor where they are activated by phosphorylation. Activated Smad2 or Smad 3 may bind to Smad 4 and be transported from the cytoplasm to the nucleus. Smad 3 and Smad 4 have been shown to bind specific DNA sequences (31), including sequences in promoters that are activated by TGF-β.

In the experiments described below, evidence that Hsp90 is overexpressed in scleroderma fibroblasts is presented. It was shown, additionally, that Hsp90 overexpression induces the activity of a collagen reporter. Each of three different heat shock overexpression constructs caused a similar induction of collagen promoter activity. Since these three heat shock proteins are also part of a complex that binds the steroid hormone receptor, it is interesting that all three induce collagen. Also shown was that heat shock per se causes a similar induction of endogenous collagen expression in 3T3 cells. In addition, Hsp90 overexpression reduced the transcription of a reporter driven by the human MMP1 promoter. These effects show that Hsp90 overexpression has a physiological role in the accumulation of collagen in scleroderma, either by inducing its production or reducing its degradation.

An increased level of binding of heat shock factor 1 (HSF1) to the consensus HSF1 binding site in scleroderma fibroblasts was also found. The HSF1 transcription factor is activated by a variety of stresses, including heat, whereupon it forms a homotrimer polypeptide and migrates to the nucleus. In the nucleus, it binds to promoters of several heat shock proteins and activates their transcription. Whether increased activity of this transcription factor is responsible for the increased levels of Hsp90 mRNA in scleroderma fibroblasts is unknown, however, since other stress-induced transcription factors may play a more important role in Hsp90 transcription. Nonetheless, it is interesting that scleroderma cells appear to activate HSF1 more readily than healthy cells after the brief 1.5 hour heat shock treatment.

These experiments also show that Hsp90 overexpression or inhibition, respectively, enhances or blocks TGF-β signal transduction. This is relevant to the scleroderma condition since high TGF-β levels have been found in the bronchial alveolar lavage fluid of scleroderma patients with pulmonary fibrosis (32), and elevated levels of the TGF-β receptor (both types I and II) have been described in scleroderma fibroblasts (33). Evidence is also provided here that Hsp90 acts on the TGF-β pathway by altering Smad function. Finally, through a combination of a new method of mouse tail vein injection with an overexpression/reporter-promoter system, in vivo evidence is generated that Hsp90 stimulates the TGF-β signal transduction pathway.

Experimental Procedures

Cell Culture, RNA Isolation

Patient biopsies, fibroblast culture and RNA isolation were performed as previously described (10). Biopsies were taken with patient consent and the approval of the Institutional Review Board for Human Studies at Boston University Medical Center. Lesional skin was clinically identified and biopsies taken from the leading edge of the lesion, usually the forearm.

Hybridization to Large Array Filter Membranes

Scleroderma or healthy fibroblast polyadenylated RNA was purified from 200–500 $\mu$g of total RNA using the polyA Spin mRNA Isolation Kit from New England Biolabs (Beverly, Mass.). Version 1.0 human EST filter arrays were purchased from Genome Systems, Inc. Hybridization and washing using $^{32}$P-labeled mRNA was performed in roller bottles following the manufacturer's recommendations with the following exceptions. Two $\mu$g of polyA RNA were labeled using avian reverse transcriptase (Promega, Madison, Wis.) at 42° instead of murine reverse transcriptase. Purification of incorporated from unincorporated counts was performed as suggested in the Genome Systems' protocol. The specific activity of the probe was measured and the total amount of radioactivity in the hybridization adjusted to $1\times10^6$ cpm per ml of hybridization fluid. Five $\mu$g of Cot1 human genomic DNA (Gibco BRL, Gaithersburg, Md.) was also included in the hybridization mixture.

Hybridization was performed overnight, and washed filters were exposed to phosphoimage cassettes overnight (Molecular Dynamics, San Diego, Calif.). Because the filters were too large for the cassettes, each filter was rotated 180° and exposed a second time. Thus, the complete filter was represented by two images.

Two filters were used 6 times each to image a total of 12 mRNA samples. The filters were washed repeatedly using 15-minute soaks in 95° deionized water until the signal measured by a Geiger counter was negligible. The soak procedure was repeated 3–6 times to achieve negligible Geiger reading. The completeness of the washing procedure was confirmed by exposing washed filters to phosphoimage cassettes overnight.

The position of each spot on the filter is uniquely identified. With the position, the user can obtain an accession number and a partial sequence of the DNA clone. The manufacturer of the filter also supplies samples of the clones that were spotted on the filter. Clone intensities were determined directly from the phosphoimages using DataMachine software (34).

Sequencing and Northern Analysis

The clone corresponding to Hsp90-α was purchased as an EST from Genome Systems. The clone was originally misidentified by the manufacturer, but re-sequencing showed it to be Hsp90-α, and hybridization of the clone to the filter confirmed it was in fact Hsp90 spotted at that position in the array. Sequencing was performed at the Boston University DNA/Protein Sequencing Core. Northern analysis of Hsp90 to total RNA from scleroderma and healthy fibroblasts was performed as previously described (10).

Immunocytochemistry

A mouse monoclonal anti-Hsp90 antibody (AC88) was obtained from StressGen (Victoria, BC). Scleroderma and healthy human dermal fibroblasts were applied to chamber slides using a Cytospin apparatus and fixed for 1 minute with 4% paraformaldehyde in PBS. The AC88 antibody was diluted 1:500 in PBS with 5% dehydrated milk and incubated in the washed, fixed chambers for 1 hour at room temperature. Samples were washed 4 times (5 minutes each) with PBS and a horseradish peroxidase-conjugated sheep anti-mouse secondary antibody (Amersham, Arlington Heights, Ill.; diluted 1:3000 in PBS) was added for 30 minutes at room temperature. Chambers were washed and enzyme activity visualized using TrueBlue (Kirkegaard and Perry Laboratories, Bethesda, Md.) and following the manufacturer's protocol.

Transient Transfection and Hsp Constructs

The complete open reading frame of Hsp70, corresponding to GenBank accession number M11717, was obtained from ATCC (Manassas, Va.); The complete open reading frame of Hsp90-α, corresponding to Riken # 1127, was obtained from Riken Gene Bank with the permission of Dr. Kasunari Yokoyama (35). This is the full-length clone whose sequence matched that of the clone 'A' in FIG. 1B. The complete open reading frame of Hsp90-α, corresponding to GenBank accession number M16660, was obtained from ATCC. Each of these three open reading frames was excised and cloned into the expression pBKRSV (Stratagene, San Diego, Calif.).

Transient transfections were performed using lipofectamine (Gibco BRL) as follows: 10 $\mu$g (total) of indicated plasmid DNA was mixed with 30 $\mu$l of lipofectamine and 500 $\mu$l of serum-free DMEM (Gibco). This mixture was incubated at room temperature for 20 minutes. Ten cm dishes of sub-confluent 3T3 fibroblasts were rinsed with PBS, and 5 ml of serum free DMEM added to each dish. The DNA/lipofectamine mixture was added to each dish and incubated in the 37° $CO_2$ incubator for 4 hours. Ten ml of DMEM with 15% serum was added and plates were incubated overnight. Medium was replaced with 10% serum at 24 hours and extracts of cells were harvested at 48 hours. Cell extracts were obtained using Passive Lysis Buffer (Promega) and assays were performed according to the Promega protocol for pGL3 luciferase vectors. Protein concentrations of all extracts were determined and each luciferase reading is normalized for protein concentration.

The 4.7 kb human MMP1 promoter driving luciferase was a gift of Constance Brinckerhoff (Dartmouth Medical School) (36). The 804 bp human type I collagen promoter driving luciferase was a gift from Russel Widom (Boston University). This construct, −804hCOL-LUC, contains a region of the type I alpha1 human collagen promoter from −804 to +114 bp. The 3TP lux construct, consisting of three AP1 sites and the plasminogen activator inhibitor promoter (37,38), was a gift from Mikhail Panchenko (Boston University). The 4.5 kb protease nexin 1 promoter driving luciferase (39) was a gift from Denis Guttridge (University of North Carolina, Chapel Hill).

Geldanamycin Treatment

Geldanamycin was a generous gift of the National Cancer Institute. Geldanamycin was dissolved in dimethylsulfoxide (DMSO) and used at a final concentration of 2 μM except where indicated otherwise. DMSO without geldanamycin was added as the carrier control for all experiments using geldanamycin.

Electrophoretic Mobility Shift Assays

Nuclear extracts of 3T3 fibroblasts were obtained using standard methods (40). Protein concentrations of extracts were determined using the BCA reagent (Pierce). Double stranded oligonucleotides corresponding to the 26 bp consensus Smad binding element (SBE) were generated (31). The probes were end-labeled using $\gamma$-$^{32}$P-ATP and T4 polynucleotide kinase. Electrophoretic mobility shift assays (EMSA) were performed using 5 μg nuclear extract, 1 μl poly dI/dC (1 mg/ml), 0.1 ng of labeled probe (in 1 μl), and buffer G to achieve a final volume of 10 μl. Buffer G consists of 20 mM Hepes (pH 7.6), 100 mM KCl, 0.2 mM EDTA and 20% glycerol. Extracts and oligo were incubated 15 minutes at room temperature before adding loading buffer and running on a non-denaturing gel. Oct-1 duplex oligonucleotides were obtained from Santa Cruz Biotechnology, Inc. Incubation of the extract and labeled SBE oligonucleotides was effectively competed with 100-fold molar excess of cold nucleotide.

Double stranded oligonucleotides corresponding to the hsf1 (heat shock factor 1) binding site (5'-gcc tcg aat gtt cgc gaa gtt tcg and 5'-cga aac ttc gcg aac att cga ggc) were generated and the EMSA was performed essentially as described in Goldenberg et al. (41).

Tail Vein Injection

Tail veins of C57/Bl mice were injected with 10 μg of total DNA and TransIT lipid complex following the procedure of the TransIT manufacturer (Panvera, Madison Wis.). In brief, DNA was mixed with lipid complex, incubated at room temperature, and diluted with a volume of dilution buffer equal to 1-tenth the animal weight (e.g., 3 mls for a 30 g animal.) Mice were injected with 5 μg of the TGF-β-sensitive reporter p3TPlux and 5 μg of either a control vector (pBKRSV) or our Hsp90 overexpression vector (pBKRSVHsp90). Mouse organs were harvested within 24 hours. Liver tissue was dounce homogenized in 0.5 mls of reporter lysis buffer (Promega, Madison, Wis.). The extract was spun for 5 minutes at 4 degrees to remove insoluble material. The supernatant was assayed using the luciferase assay kit (Promega, Madison, Wis.): 5 μl of suspension was added to 100 μl of luciferase assay reagent.

The following examples are presented to illustrate the advantages of the present invention and to assist one of ordinary skill in making and using the same. These examples are not intended in any way otherwise to limit the scope of the disclosure.

EXAMPLE I

Hsp90α is Overexpressed in Scleroderma Fibroblasts

Polyadenylated mRNA was purified from healthy and diseased human dermal fibroblasts. Cells were obtained from both clinically lesional and non-lesional skin of four systemic sclerosis patients and from 4 healthy individuals. Radioactive labeled cDNA made from the mRNA was used to probe commercially available filters containing 18,432 pairs of robotically spotted DNA samples (FIG. 1A). Filters were exposed to phosphoimage plates, and, initially, a visual inspection was performed to identify positions of clones that were differentially expressed in scleroderma fibroblasts. More than 30 clones were found that were apparently overexpressed in scleroderma fibroblasts and more than 30 that were expressed more highly in the healthy lines. Eighteen of these clones were purchased and sequenced. Approximately half of these 18 sequences did not match the putative sequences predicted by the supplier. (However, when these clones were labeled and hybridized to the original filter, 17 of them hybridized to the appropriate position.)

FIG. 1B shows a pattern of clones consistently overexpressed in scleroderma fibroblasts. The Figure shows the same region of filters that had been probed either with mRNA from healthy dermal fibroblasts (panels N-96-05, N-96-02 and N-92-04) or mRNA from lesional scleroderma fibroblasts (panels 96-02-A, 97-03-A and 97-02-A). The panels show two clones (4 spots) which are not differentially expressed, labeled R, or reference clones. The panels also show three clones that are much more highly expressed in the scleroderma fibroblasts. These three pairs of spots are designated A, B and C. Clone A was sequenced and its sequence corresponded to heat shock protein 90 alpha (Hsp90α).

Northern analysis of total RNA from cultured scleroderma and healthy human dermal fibroblasts verified the differential expression predicted by the filter array results. FIG. 2 shows the northern results. Lesional scleroderma lines were derived from biopsies of areas of patients' skin that contained phenotypically thickened tissues. Non-lesional scleroderma lines are derived from biopsies of areas of patients' skin that were phenotypically healthy. The northern analysis shows that Hsp90 is overexpressed in both lesional (L) and non-lesional (N) fibroblasts derived from biopsies of three independent scleroderma patients (P1, P2, and P3). Only one of the 6 lines derived from biopsies of healthy individuals (N1–N6) exhibited any Hsp90 signal.

Figure 3:
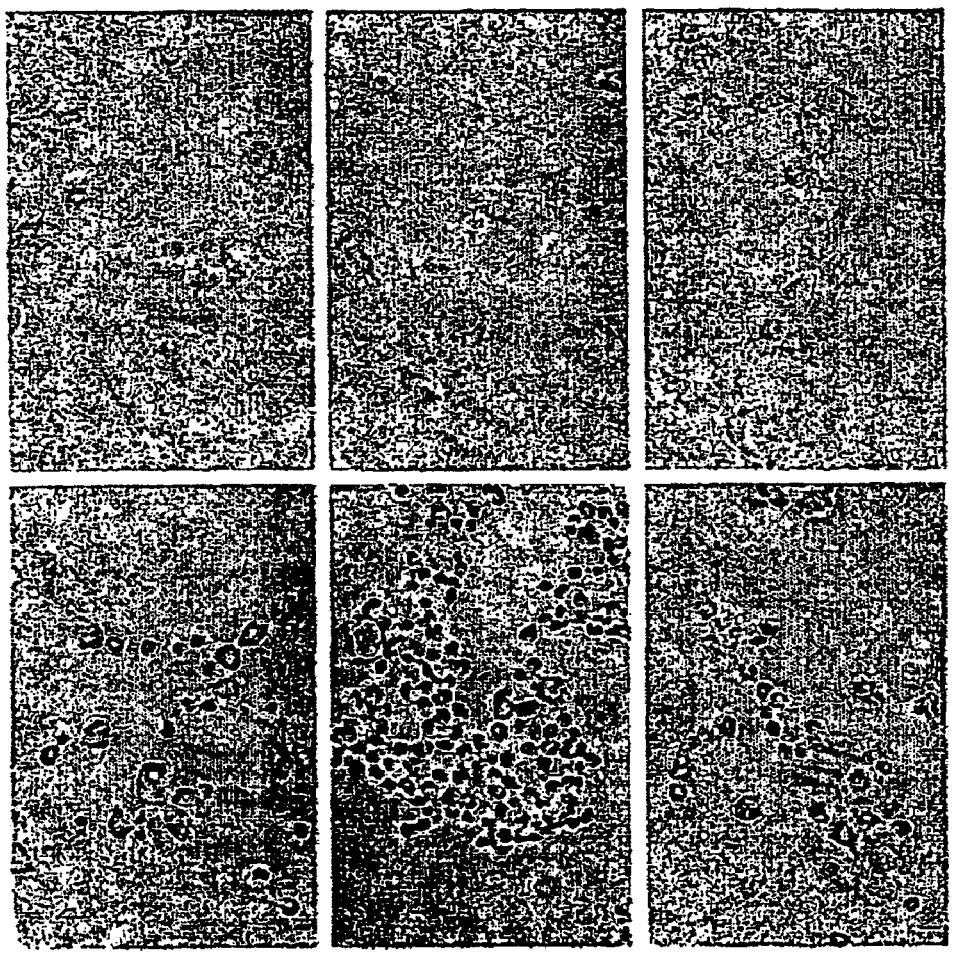
FIG. 3 shows use of a mouse monoclonal anti-Hsp90 antibody to visualize Hsp90 protein in three healthy fibroblast lines (A–C) or in three scleroderma fibroblast lines (D–F)

Immunocytochemistry on cultured scleroderma and healthy human dermal cells showed that Hsp90 protein levels reflected the differential expression of the MRNA. FIG. 3 shows immunocytochemical staining of three healthy human dermal lines (panels A, B, C) and three lesional scleroderma fibroblast lines (panels D, E, F) using a monoclonal anti-HSP90 antibody, AC88. The scleroderma lines showed intense staining while the healthy lines showed little if any signal.

In addition to examining the expression of Hsp90 in scleroderma and healthy human dermal fibroblasts, the expression and activity of the factor thought to be of primary importance in the induction of heat shock proteins, heat shock factor 1 (HSF1) (41) was examined. This cytoplasmic protein responds to heat shock by forming a trimer and translocating to the nucleus, where it binds heat shock sensitive elements to regulate transcription (42,43).

Figure 4:
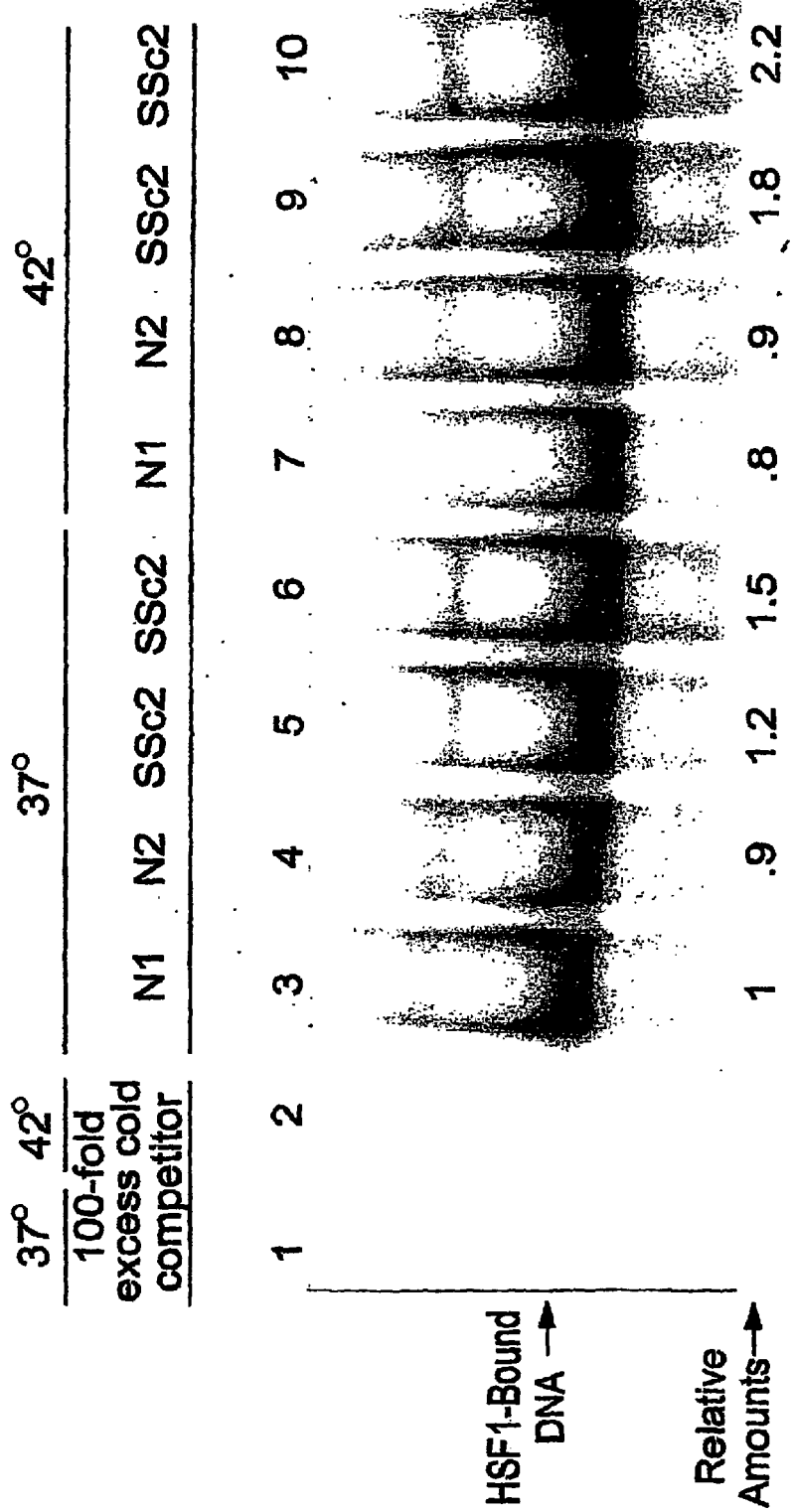
FIG. 4 shows human dermal fibroblasts (healthy and scleroderma) plated in equal numbers and cultured overnight. Where indicated, cells were heat shocked at 42° for 1.5 hours. Nuclear extracts were prepared and bound to labeled duplex oligos as described in Experimental Procedures. Protein concentrations were determined for each sample and equal amounts of protein was bound and loaded onto the gel.

The amount of HSF1 DNA binding activity was determined by performing EMSA assays on two different healthy dermal fibroblast lines and on two different scleroderma fibroblast lines. DNA binding sequences were synthesized based on previously published HSF1 DNA binding data (41). The results show that the basal level of HSF1 DNA binding activity in the nucleus of scleroderma cells is slightly higher than that in healthy fibroblasts (FIG. 4, lanes 2–5). However, the level of HSF1 DNA binding activity after a brief, 1.5 hour, heat shock at 42° is 144% higher in scleroderma cells (FIG. 4, lanes 7–10). In the brief heat shock period used, there was no significant increase in the HSF1 DNA binding activity in the healthy cells. There was, however, a 48% increase in the level of HSF1 DNA binding activity in the scleroderma cells with heat shock. These results suggest that scleroderma cells exhibit both a higher basal level of HSF1DNA binding activity and an increased induction of this activity with heat shock.

EXAMPLE II

Hsp90 Overexpression Induces Collagen and Represses Collagenase

Figure 5:
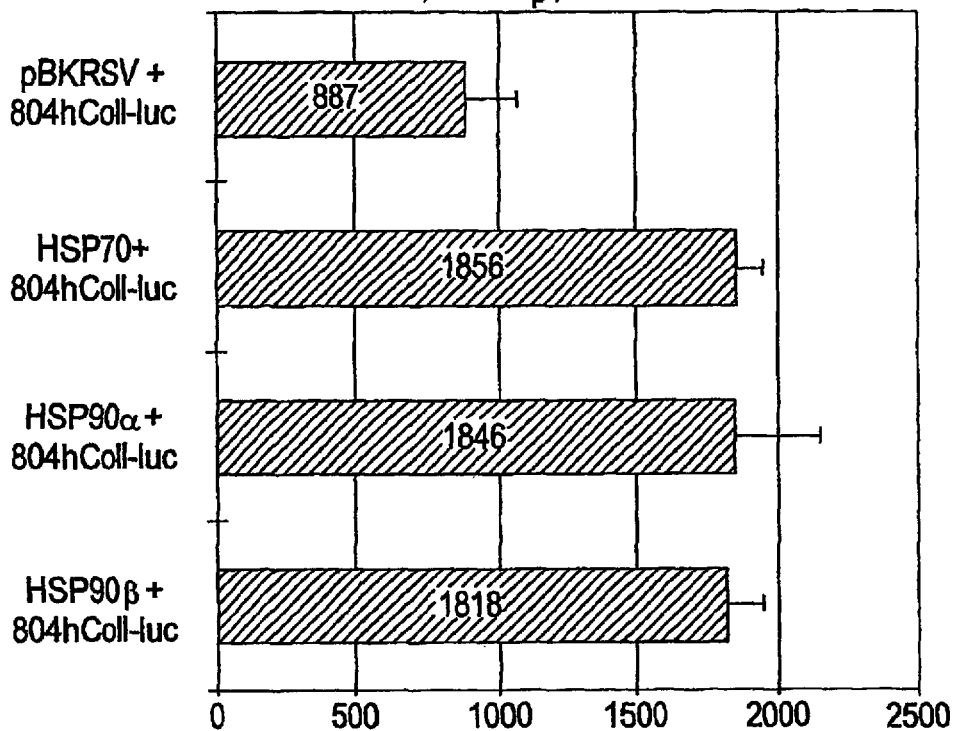
FIG. 5 shows NIH 3T3 fibroblasts co-transfected with an 804 bp proximal region of the collagen 1 α (I) promoter driving luciferase and either an empty control vector (pBKRSV), an Hsp70 overexpression plasmid, an Hsp90-α overexpression plasmid or an Hsp90-β overexpression plasmid. Transfections were performed in triplicate and each extract was assayed in duplicate. Extracts were harvested and normalized to the protein concentration in each extract.

Collagen transcription activity was examined in a co-transfection assay utilizing an 804 bp proximal region of the human type I collagen promoter driving a luciferase reporter. Hsp90-α, Hsp90-β, Hsp70 overexpression constructs or an empty vector control were co-transfected with the collagen promoter/reporter. FIG. 5 shows that in mouse NIH 3T3 fibroblasts each of the three heat shock genes caused more than a 2-fold increase in collagen promoter activity compared to the empty vector which serves as the backbone for the overexpression constructs. The bars represent data from three transfections, each assayed in duplicate.

Figure 6:
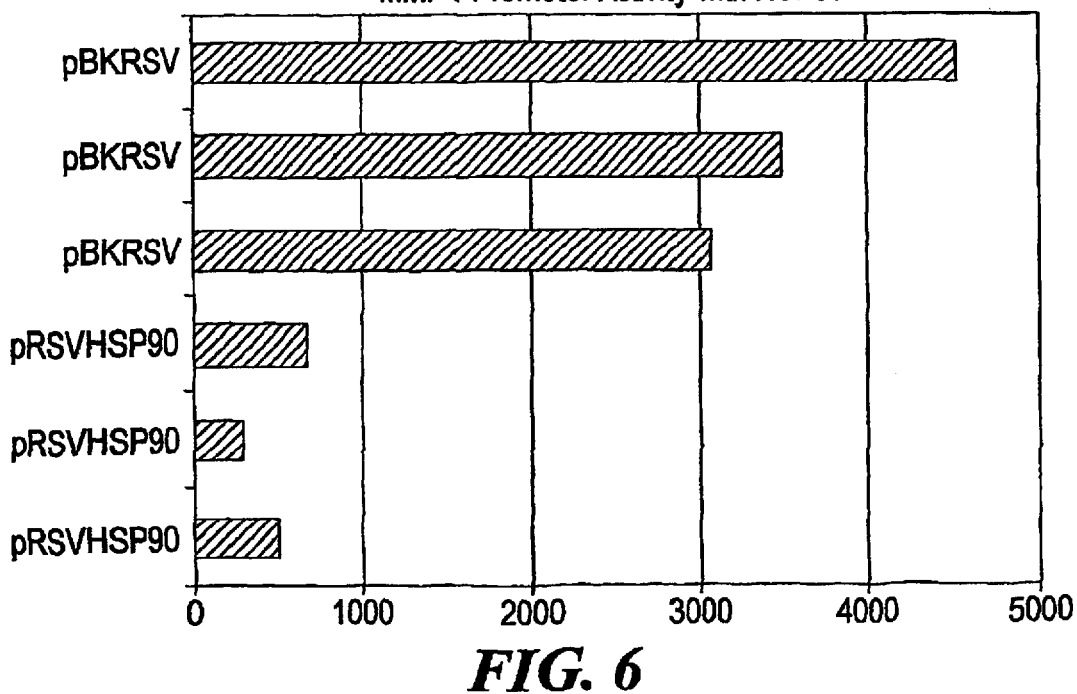
FIG. 6 shows NIH 3T3 fibroblasts co-transfected with a 4.7 kb region of the human collagenase (MMP1) promoter driving a luciferase reporter and either an empty control vector (pBKRSV) or an Hsp90-β overexpression plasmid. Transfections were performed in triplicate and each extract was assayed in duplicate. Extracts were harvested and normalized to the protein concentration in each extract.

Net matrix accumulation in scleroderma might be caused either by increased synthesis or decreased degradation of collagen. FIG. 6 shows the results of an experiment designed to examine whether overexpression of Hsp90 had reciprocal effects on collagen and collagenase (human MMP1) expression. Co-transfection of Hsp90-α with a 4.7 kb fragment of the human MMP1 promoter driving luciferase shows that Hsp90 caused an 8-fold decrease in collagenase promoter activity in 3T3 fibroblasts. These results also indicate that Hsp90 overexpression does not indiscriminately activate promoters. Rather, Hsp90 both activates and represses different promoters in the same cell line.

EXAMPLE III

Figure 7A:
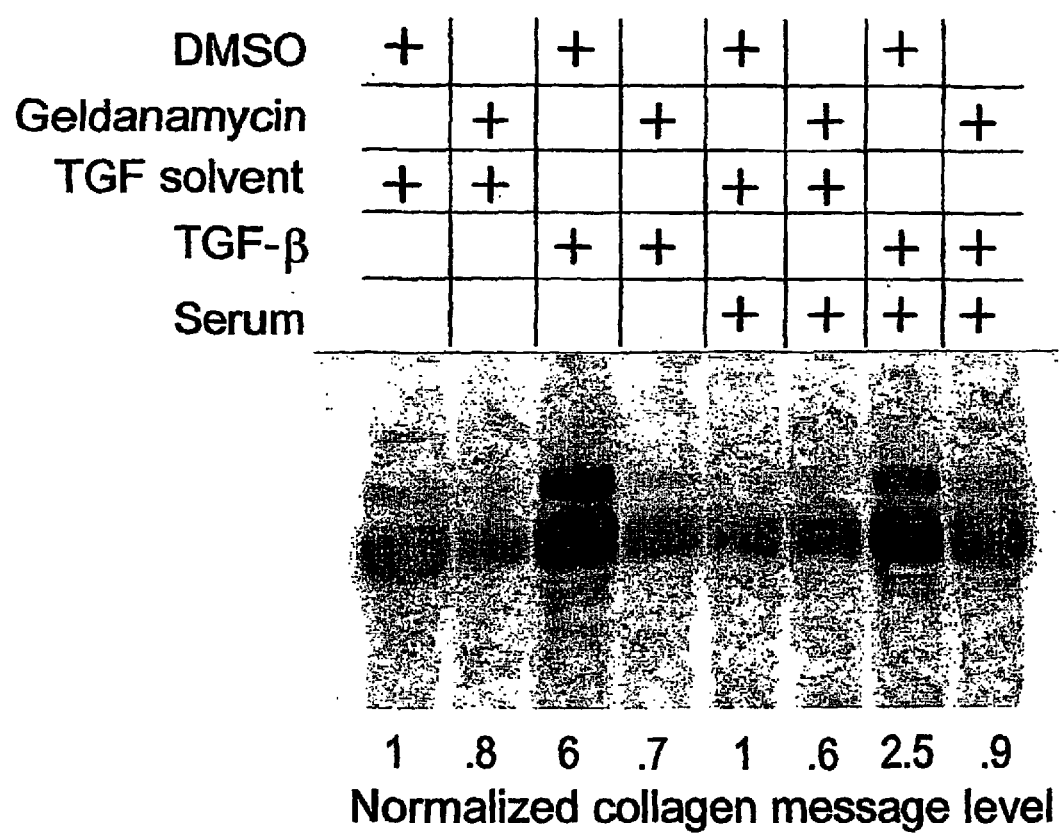
FIGS. 7A–7C show fibroblasts subjected to 24-hour treatments with geldanamycin, TGF or both. After 24 hours, total RNA was harvested and subjected to northern analysis using an α1(I) collagen probe. (A) Northern analysis using NIH 3T3 fibroblasts. (B) Northern analysis using primary healthy human dermal fibroblasts. (C) Methylene blue staining of the filter in (B). Numbers represent relative intensities of the lower collagen band after normalizing bands to GAPDH band intensity.
Figures 7B, 7C:
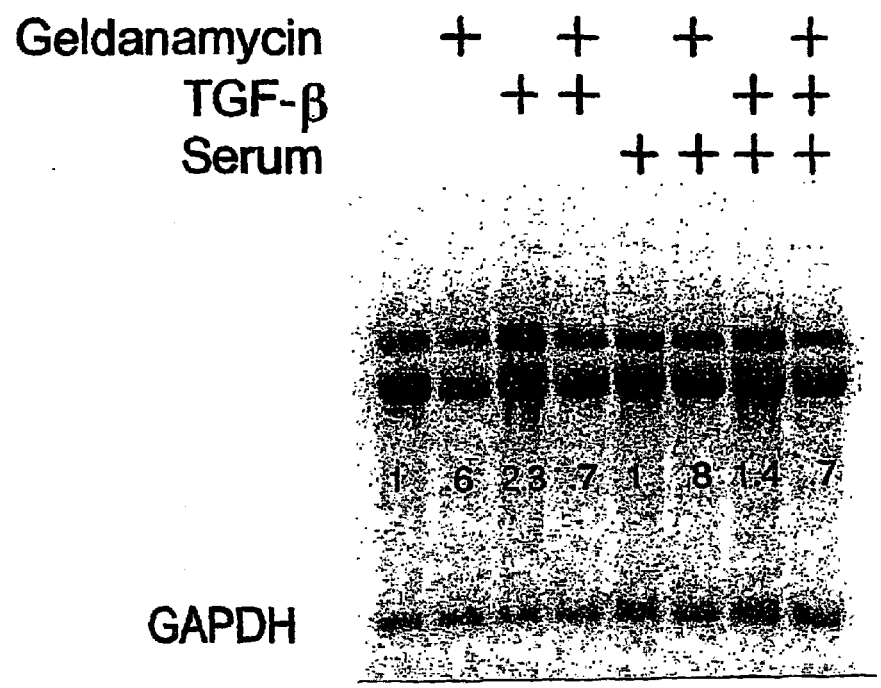

Geldanamycin Inhibits Basal Collagen Synthesis and TGF-β-induced Collagen Promoter Activation The chaperone function of Hsp90 is dependent on the hydrolysis of ATP (44). Geldanamycin, a benzoquinone ansamycin antibiotic, specifically inhibits Hsp90 by binding to its ATP binding site (18). Geldanamycin was examined to determine whether its inhibition of Hsp90 affected TGF-β activation of collagen transcription in mouse 3T3 and human dermal fibroblasts. Endogenous collagen message levels were used as a measure of TGF-β signal transduction. The northern blots in FIG. 7 shows the effect of geldanamycin on collagen message levels in the absence or presence of TGF-β. The top panel (FIG. 7A) shows the effect in mouse 3T3 cells and the middle panel (FIG. 7B) in healthy human dermal fibroblasts. The left 4 lanes of this panel show, in the absence of serum, that geldanamycin reduces the basal level of the collagen transcript. With TGF-β, the level of the endogenous collagen transcript is increased approximately 6-fold. However, when geldanamycin and TGF-β are added together, the inhibitory effect of geldanamycin dominates. Thus, despite the 6-fold increase in collagen due to TGF-β, the addition of geldanamycin still reduces the collagen transcript level below baseline. The results in the presence of serum (right 4 lanes) are similar. The endogenous collagen transcript shows only a 2-fold increase with TGF-β in the presence of serum, presumably because cells have already acclimated to TGF-β or a related stimulus in the serum itself. However, geldanamycin alone or geldanamycin in the presence of TGF-β still causes a reduction of collagen transcript to below baseline.

The middle panel (FIG. 7B) shows an analogous experiment using primary cultured healthy human dermal fibroblasts. Although the induction of collagen in human cells by TGF-β is reduced, the results follow the same trends as with mouse 3T3 fibroblasts. As before, geldanamycin alone reduces collagen synthesis and the induction of collagen by TGF-β is completely blocked by geldanamycin. This panel also shows a control hybridization of the blot using a labeled GAPDH probe. The GAPDH message level showed no variation, either with TGF-β or with geldanamycin. As shown in the bottom panel (FIG. 7C), the same filter was also stained with methylene blue to identify RNA before hybridization. This staining revealed the 28 S and 18 S ribosomal bands as indicated, along with a faint smear which represents the rest of the RNA in each lane. As with the GAPDH, there was no indication of non-specific changes in message level either with the addition of geldanamycin, TGF-β or both. These controls suggest that the effect of geldanamycin on collagen message level is not a result of a general toxicity.

EXAMPLE IV

Geldanamycin Blocks the TGF-β-activated 3TP-lux Promoter and Has No Effect on the PN1 Promoter Since geldanamycin blocked the activation of the collagen promoter by TGF-β, the effect of geldanamycin on other promoters sensitive or insensitive to TGF-β was investigated. Mouse NIH 3T3 cells were tranfected with the 3TPlux vector, which is known to be very sensitive to TGF-β, or a vector that contains a 4.5 kb portion of the protease nexin 1 promoter driving luciferase. The PN1 promoter has not previously been shown to exhibit any sensitivity to TGF-β. However, previous studies had shown that PN1 is overexpressed in scleroderma fibroblasts and in scleroderma skin (10). Transfected cells were exposed to a 24 hour treatment of geldanamycin, TGF-β or both. Cells were then harvested and assayed for luciferase activity.

Figure 8:
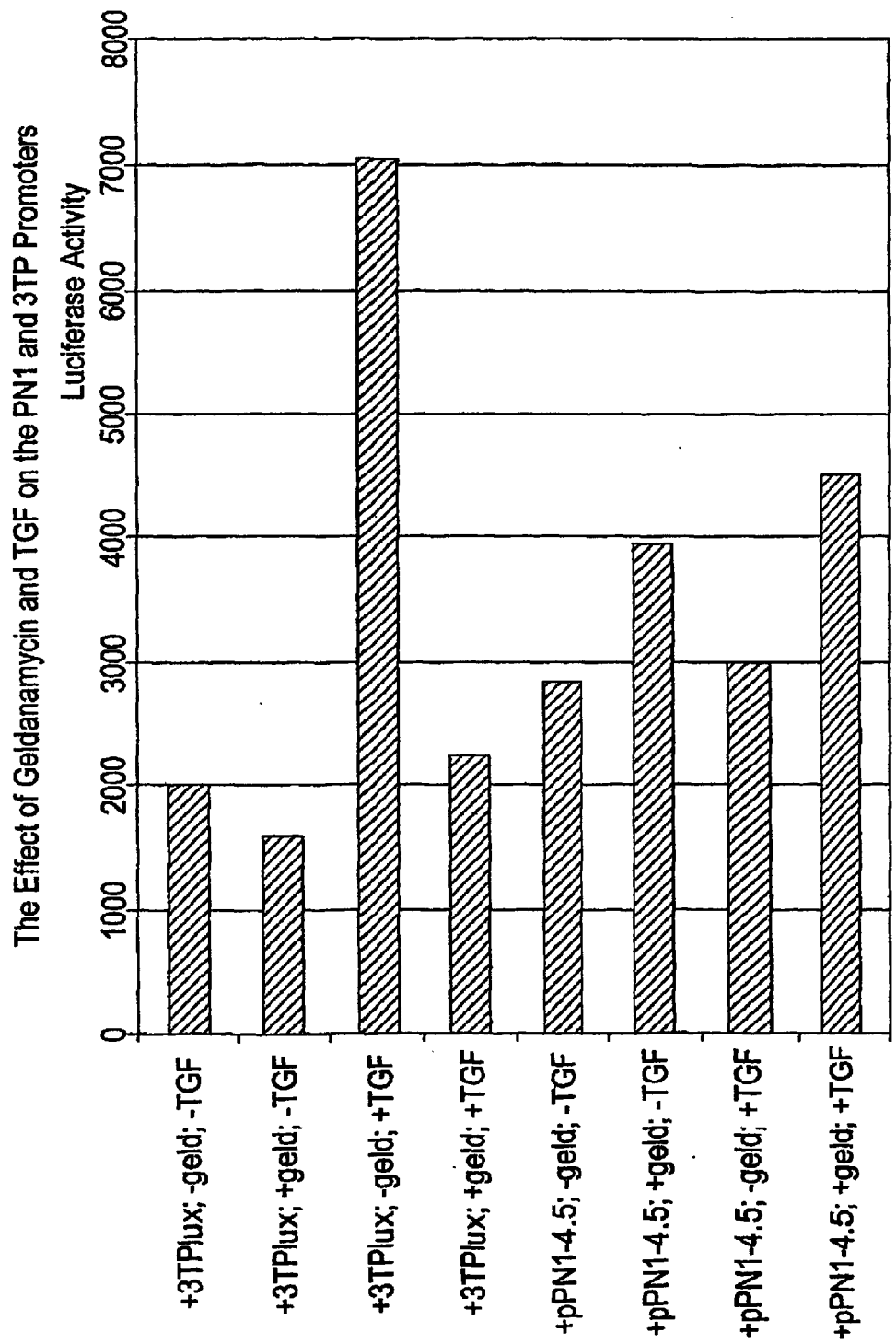
FIG. 8 shows NIH 3T3 fibroblasts transfected with either the TGF-sensitive reporter p3TPlux or pPN1–4.5. The latter contains a 4.5 kb fragment of the PN1 promoter driving the luciferase gene. Cells were incubated for 24 hours after transfection, washed 3 times with PBS and then subjected to a 24 hour treatment with geldanamycin, TGF or both, as indicated. Cells were then harvested and luciferase activities determined.

FIG. 8 shows that the addition of geldanamycin slightly reduces the level of expression of the TGF-β-sensitive promoter in the 3TPlux construct. As expected, TGF-β by itself resulted in a 3.5-fold induction of the activity of this promoter. This induction, however, was completely blocked when geldanamycin and TGF-β were added simultaneously. The FIG. also shows that TGF-β has little effect on the expression of the PN1 promoter. Geldanamycin neither reduces the basal level of activity of this promoter nor reduces the activity of this promoter in the presence of TGF-β. In fact, it seems that geldanamycin may exert a small induction on the activity of the PN1 promoter.

These results, together with the data on collagen promoter inhibition in FIG. 7, suggest that the effect of geldanamycin on promoter inhibition is somewhat specific for promoters that are activated by TGF-β. Neither the PN1 nor the GAPDH promoters are blocked by the addition of geldanamycin. However, the TGF-β-sensitive promoters in the 3TPlux construct and the collagen gene are both subject to inhibition by geldanamycin. These facts led to a consideration of whether Hsp90 overexpression or geldanamycin inhibition of Hsp90 may function on the TGF-β signaling pathway.

EXAMPLE V

Hsp90 Induces the Expression of p3TP-lux When Transiently Expressed in vivo

To investigate further the role of Hsp90 in TGF-β signal transduction, a novel method of tail vein injection was employed. Tail vein injection of either naked DNA or DNA complexed in lipophilic moieties results in high levels of expression of the transgene in internal organs, most prominently in the liver (45–47). Expression levels peak between 8 and 24 hours after injection, making this a rapid method to assess gene activity in vivo without resorting to the use of a large number of mice as required in traditional transgenic studies.

While previous studies examined the expression of a single reporter, this study expanded that work by co-injecting both a promoter-reporter and an overexpression plasmid. In this study, 5 μg of TGF-β-sensitive reporter plasmid (p3TP-lux) was co-injected with 5 μg of either an empty control vector (pBKRSV) or a plasmid that overexpresses Hsp90-α (pBKRSVHsp90). Generally, 3 ml of a DNA-lipophilic agent mixture were injected as detailed in Experimental Procedures.

Figure 9:
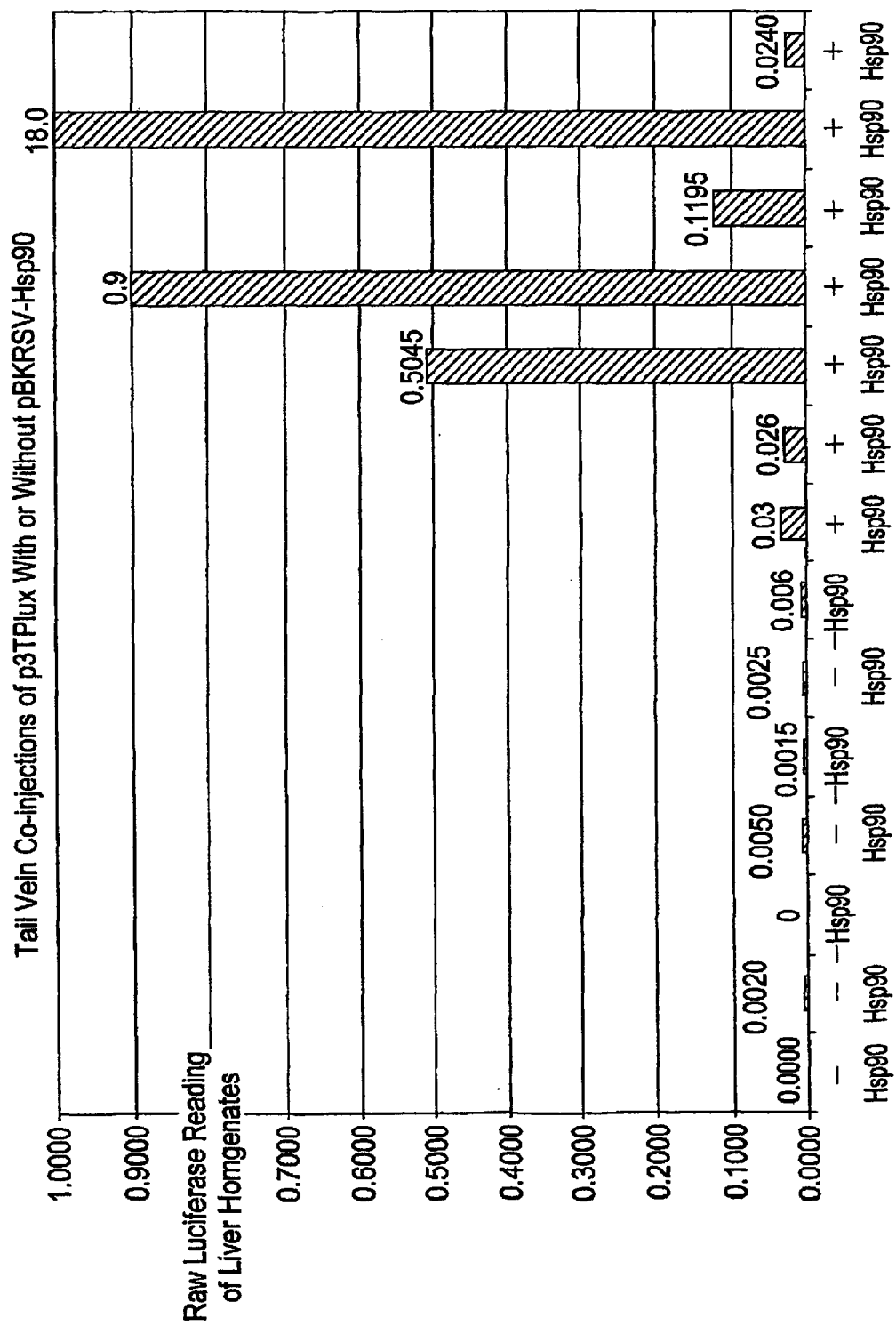
FIG. 9 shows Hsp90 stimulating the expression of 3TP lux in transiently transfected transgenic mice. Mice were injected in the tail vein with either the 3TPlux reporter and an Hsp90 overexpression vector or the reporter and a pBKRSV empty vector control. Animal livers were harvested at approximately 16 hours after injection and extracted in luciferase reporter buffer as described in Experimental Procedures. Each bar represents the luciferase activity from a single mouse. All readings were made in duplicate from a single liver extract. The actual data values for each injection are shown. No significant activity was found in any animal injected with the control.

In pilot studies, luciferase activities were measured in extracts from heart, lung, thymus, liver, kidney and spleen. There was very low expression in all organs except liver. In subsequent experiments, luciferase activity was measured only in extracts of liver tissue, and always within 16–24 hours after the injection. FIG. 9 shows that the 3TPlux reporter was significantly expressed only when Hsp90 was co-expressed with the reporter. Hsp90 expression induced the reporter by at least five-fold in all cases. In some cases, Hsp90 induced the reporter several hundred fold. These results complement the earlier data, which demonstrate that inhibiting Hsp90 blocks 3TPlux expression (FIG. 8) and blocks the TGF-β response of the endogenous collagen gene (FIG. 7). Further studies should reveal whether the overexpression of Hsp90 in the liver also induces the expression of endogenous transcripts that are activated by TGF-β.

EXAMPLE VI

Figure 10:
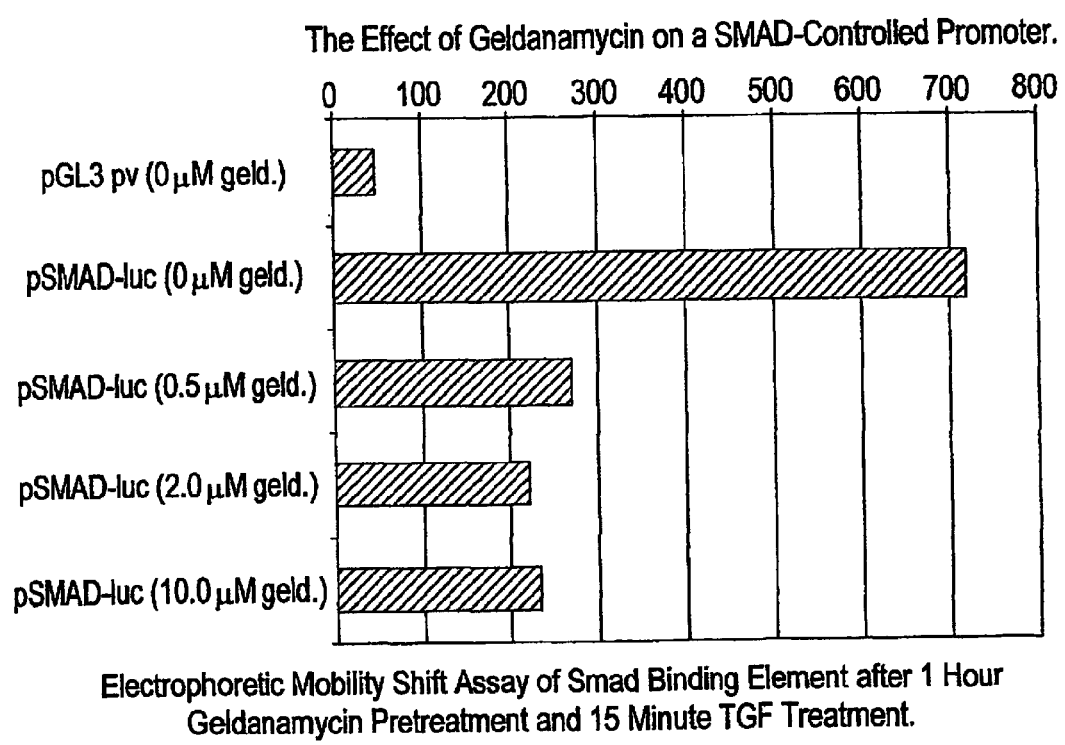
FIG. 10 shows NIH 3T3 cells transfected with either the pGL3 promoter vector (containing a minimal promoter driving a luciferase reporter) or the pGL3 promoter vector containing a Smad binding element. The specific Hsp90 inhibitor, geldanamycin, was added four hours after the initiation of the transfection and replaced with fresh drug and medium at 24 hours. Cells were harvested at 48 hours, protein concentrations of extracts determined and luciferase activity measured. Values shown are luciferase activities normalized to protein concentration.

Geldanamycin Inhibits Activation of a Smad-controlled Promoter and Decreases Smad DNA Binding To examine whether the effect of geldanamycin was exerted on Smads, the signal transduction protein for TGF-β, a Smad controlled reporter plasmid, was constructed identically to a previously reported vector (31). Smad 3 and Smad 4 bind to specific sequences which were cloned into the pGL3 luciferase reporter vector, which otherwise had a minimal promoter. The Smad-controlled reporter or the pGL3pv control plasmid were transfected into 3T3 fibroblasts in the presence or absence of increasing concentrations of geldanamycin. FIG. 10 demonstrates that Smad binding sequences cause a dramatic increase in reporter transcription even in the absence of exogenously supplied TGF-β. This suggests that 3T3 fibroblasts have a considerable baseline level of active Smad, a finding that has also been reported in melanoma cells (48). Geldanamycin reduced Smad-dependent transcription by two-thirds. This suggests that geldanamycin prevents the Smad signaling by either preventing the activation of Smad or preventing translocation of active Smad to the nucleus.

Figure 11A:
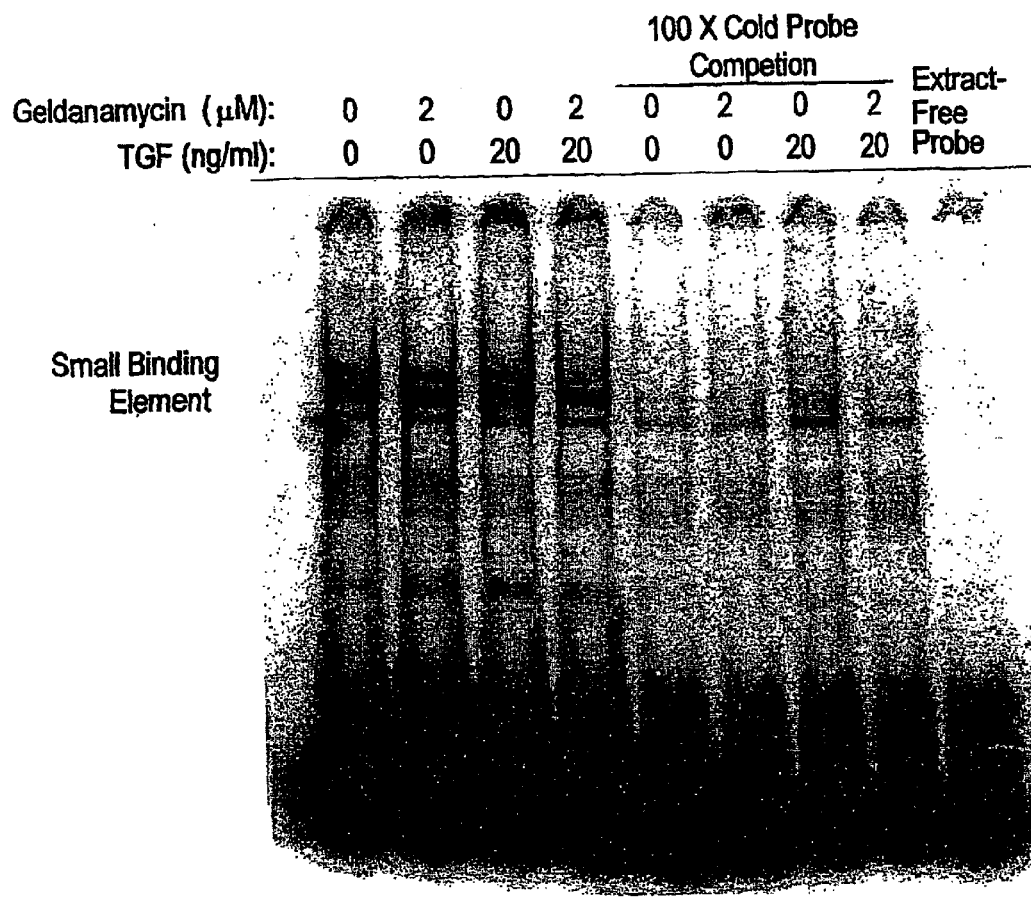
FIGS. 11A–11B show NIH 3T3 fibroblasts treated for 1 hour with the indicated concentration of geldanamycin and then 15 minutes with TGF-β where indicated. (A) Cells were harvested and subjecting to electrophoretic mobility shift analysis using a Smad binding element (SBE). Relative band intensities are shown. Where indicated, extracts were prepared with 100-fold higher levels of cold competitor probe. (B) Cells were subjected to 24 hour treatments with geldanamycin at various concentrations and extracts prepared and bound to control Oct-1-binding duplex oligos to monitor non-specific effects of geldanamycin.
Figure 11B:
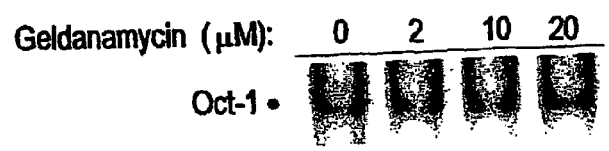

Electrophoretic mobility shift assays were performed to examine whether geldanamycin reduced the level of Smad DNA-binding activity in nuclear extracts. As before, cells were also subjected to TGF-β or TGF-β and geldanamycin together. In this experiment (FIG. 11A), cells were pretreated for 1 hour with geldanamycin and then given a brief, 15-minute treatment with TGF-β prior to harvesting nuclear extracts for binding. The level of Smad bound to its Smad binding element was modestly reduced relative to control by the 1 hour treatment with 20 μM geldanamycin (compare the first and second lanes). TGF-β, as expected, caused a modest increase in nuclear Smad after a 15 minute treatment. This level of increase, however, was reduced to below the control by the treatment with geldanamycin before the addition of TGF-β (fourth lane). By contrast, the level of binding of Smad from 3T3 nuclear extracts to the Oct1 binding site (FIG. 11B) was not significantly changed in any of the concentrations of geldanamycin during a 24 hour treatment.

Use

The results reported here show that compounds capable of interfering with the activity of a collagen promotor are good candidates for prophylaxis or treatment of scleroderma and other fibrogenic diseases or disorders. The Hsp90-α chaperone function inhibitors described above have been shown to be strong inhibitors of TGF-β-induced expression of reporters under the control of the collagen promoter. Therefore, they will be very useful in therapeutic compositions and methods for treating patients with, or believed to be at risk of acquiring, fibrogenic disorders. The therapeutic compositions may be administered topically, orally, or parenterally, (e.g., intranasally, subcutaneously, intramuscularly, intravenously, or intra-arterially) by routine methods in pharmaceutically acceptable inert carrier substances. For example, the therapeutic compositions of the invention may be administered locally by direct application in a carrier vehicle, by on-site delivery using micelles, gels or liposomes, or in a sustained release formulation using a biodegradable biocompatible polymer. The therapeutic agents can be administered, e.g., locally, in a dosage of 0.05 μg/kg/day to 10 μg/kg/day (and preferably 0.25 μg/kg/day to 2.5 μg/kg/day) for a total of, e.g., 50 μg/day for a 70 kg human patient. Optimal dosage and modes of administration can readily be determined by conventional protocols.

Preferred inhibitors according to the invention include known inhibitors of Hsp90-α function, and in particular, geldanamycin. Since geldanamycin is a small organic molecule, it is readily amenable to a number of modifications, as is well known to those of ordinary skill in the art. Such modifications can include, but not be limited to, additions of carbonyl, amine, hydroxyl and other groups to the reactive sites already on geldanamycin, including the oxygen and nitrogen positions. The purpose of such modifications is, e.g., to enhance drug uptake in human and animal systems as well as to enhance the effectiveness of the drug in blocking the TGF-β signaling pathway and in blocking the production of collagen and other matrix components.

Three systems that can be used to measure the effectiveness of such modifications or, in general, to screen candidate inhibitors, include:

(1) A mouse fibroblast-derived cell line stably transfected with a TGF-β-responsive promoter driving a luciferase reporter (p3TP-lux). Such a cell line gives a 10–30-fold increase in luciferase activity in response to TGF-β. This increase is known to be substantially blocked by geldanamycin, and the effectiveness of a candidate inhibitor can be compared to the activity of geldanamycin as a positive control.

(2) Mouse and human cell lines stably transfected with a collagen promoter driving luciferase and/or green fluorescent protein reporters. These cell lines can be used to demonstrate the effect of geldanamycin, its derivatives and related candidate inhibitors of Hsp90 in blocking the TGF-β-induced expression of reporters under the control of the collagen promoter.

(3) Northern analysis of endogenous collagen message can be can be carried out on healthy human dermal fibroblasts to measure the effect of geldanamycin, derivatives and related inhibitors on the transcription of the endogenous collagen message.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

REFERENCES

1. Medsger, T. A., Jr. (1994) *Clinics in Dermatology* 12(2), 207–16.
2. Tan, F. K., Stivers, D. N., Arnett, F. C., Chakraborty, R., Howard, R., and Reveille, J. D. (1999) *Tissue Antigens* 53(1), 74–80.
3. Tan, F. K., Stivers, D. N., Foster, M. W., Chakraborty, R., Howard, R. F., Milewicz, D. M., and Arnett, F. C. (1998) *Arthritis Rheum* 41(10), 1729–37.
4. Siracusa, L. D., McGrath, R., Ma, Q., Moskow, J. J., Manne, J., Christner, P. J., Buchberg, A. M., and Jimenez, S. A. (1996) *Genome Res* 6(4), 300–13.
5. Bona, C. A., Murai, C., Casares, S., Kasturi, K., Nishimura, H., Honjo, T., and Matsuda, F. (1997) *DNA Res* 4(4), 267–71.
6. Arnaiz-Villena, A., Martinez-Laso, J., Corell, A., Allende, L., Rosal, M., Gomez-Reino, J. J;, and Vicario, J. L. (1996) *Eur J Immunogenet* 23(3), 211–9.
7. Black, C., Pereira, S., McWhirter, A., Welsh, K., and Laurent, R. (1986) *J Rheumatol* 13(6), 1059–62.
8. Vuorio, T. K., Kahari, V. M., Lehtonen, A., and Vuorio, E. I. (1984) *Scandinavian Journal of Rheumatology* 13(3), 229–37
9. Krieg, T., Braun-Falco, O., Perlish, J. S., and Fleischmajer, R. (1983) *Archives of Dermatological Research* 275(6), 393–6.
10. Strehlow, D., Jelaska, A., Strehlow, K., and Korn, J. H. (1999) *The Journal of Clinical Investigation* 103(8), 1179–1190.
11. Feghali, C. A., and Wright, T. M. (1996) *Arthritis & Rheumatism* 39(9 (Supplement)), S318.
12. Jakob, U., Lilie, H., Meyer, I., and Buchner, J. (1995) *J Biol Chem* 270(13), 7288–94.
13. Nathan, D. F., and Lindquist, S. (1995) *Mol Cell Biol* 15(7), 3917–25.
14. Fang, Y., Fliss, A. E., Robins, D. M., and Caplan, A. J. (1996) *J Biol Chem* 271(45), 28697–702.
15. Pratt, W. B., and Welsh, M. J. (1994) *Semin Cell Biol* 5(2), 83–93.
16. Galigniana, M. D., Scruggs, J. L., Herrington, J., Welsh, M. J., Carter-Su, C., Housley, P. R., and Pratt, W. B. (1998) *Mol Endocrinol* 12(12), 1903–13.
17. Kosano, H., Stensgard, B., Charlesworth, M. C., McMahon, N., and Toft, D. (1998) *J Biol Chem* 273(49), 32973–9.
18. Roe, S. M., Prodromou, C., O'Brien, R., Ladbury, J. E., Piper, P. W., and Pearl, L. H. (1999) *J Med Chem* 42(2), 260–6
19. Knoblauch, R., and Garabedian, M. J. (1999) *Mol Cell Biol* 19(5), 3748–59.
20. Pratt, W. B. (1987) *J Cell Biochem* 35(1), 51–68.
21. Perdew, G. H. (1988) *J Biol Chem* 263(27), 13802–5.
22. Denis, M., Cuthill, S., Wikstrom, A. C., Poellinger, L., and Gustafsson, J. A. (1988) *Biochem Biophys Res Commun* 155 (2), 801–7.
23. Dougherty, J. J., Rabideau, D. A., Iannotti, A. M., Sullivan, W. P., and Toft, D. O. (1987) *Biochim Biophys Acta* 927(1), 74–80.
24. Brugge, J. S., Erikson, E., and Erikson, R. L. (1981) *Cell* 25(2), 363–72.
25. Rose, D. W., Wettenhall, R. E., Kudlicki, W., Kramer, G., and Hardesty, B. (1987) *Biochemistry* 26(21), 6583–7.
26. van der Straten, A., Rommel, C., Dickson, B., and Hafen, E. (1997) *Embo J* 16(8), 1961–9.
27. Cutforth, T., and Rubin, G. M. (1994) *Cell* 77(7), 1027–36
28. Roberts, A. B., and Sporn, M. B. (1993) *Growth Factors* 8(1), 1–9.
29. Lagna, G., Hata, A., Hemmati-Brivanlou, A., and Massague, J. (1996) *Nature* 383(6603), 832–6.
30. Baker, J. C., and Harland, R. M. (1997) *Curr Opin Genet Dev* 7(4), 467–73.
31. Zawel, L., Dai, J. L., Buckhaults, P., Zhou, S., Kinzler, K. W., Vogelstein, B., and Kern, S. E. (1998) *Mol Cell* 1(4), 611–7.
32. Ludwicka, A., Ohba, T., Trojanowska, M., Yamakage, A., Strange, C., Smith, E. A., Leroy, E. C., Sutherland, S., and Silver, R. M. (1995) *J Rheumatol* 22(10) , 1876–83.
33. Kawakami, T., Ihn, H., Xu, W., Smith, E., LeRoy, C., and Trojanowska, M. (1998) *J Invest Dermatol* 110(1), 47–51.
34. Strehlow, D. (2000) *Biotechniques* 29, 118–121.
35. Yamazaki, M., Akaogi, K., Miwa, T., Imai, T., Soeda, E., and Yokoyama, K. (1989) *Nucleic Acids Res* 17(17), 7108.
36. Benbow, U., Rutter, J. L., Lowrey, C. H., and Brinckerhoff, C. E. (1999) *Br J Cancer* 79(2), 221–8.
37. Martens, J. W., de Winter, J. P., Timmerman, M. A., McLuskey, A., van Schaik, R. H., Themmen, A. P., and de Jong, F. H. (1997) *Endocrinology* 138(7), 2928–36.
38. De Winter, J. P., De Vries, C. J., Van Achterberg, T. A., Ameerun, R. F., Feijen, A., Sugino, H., De Waele, P., Huylebroeck, D., Verschueren, K., and Van Den Eijden-Van Raaij, A. J. (1996) *Exp Cell Res* 224(2), 323–34.
39. Guttridge, D. C., and Cunningham, D. D. (1996) *Journal of Neurochemistry* 67(2), 498–507.
40. Hoppe-Seyler, F., Butz, K., Rittmuller, C., and von Knebel Doeberitz, M. (1991) *Nucleic Acids Res* 19(18), 5080.
41. Goldenberg, C. J., Luo, Y., Fenna, M., Baler, R., Weinmann, R., and Voellmy, R. (1988) *J Biol Chem* 263(36), 19734–9.
42. Westwood, J. T., and Wu, C. (1993) *Mol Cell Biol* 13(6), 3481–6.
43. Rabindran, S. K., Haroun, R. I., Clos, J., Wisniewski, J., and Wu, C. (1993) *Science* 259(5092), 230-.
44. Obermann, W. M., Sondermann, H., Russo, A. A., Pavletich, N. P., and Hartl, F. U. (1998) *J Cell Biol* 143(4), 901–10.
45. Ren, T., Song, Y. K., Zhang, G., and Liu, D. (2000) *Gene Ther* 7(9), 764–8.
46. Liu, F., Song, Y., and Liu, D. (1999) *Gene Ther* 6(7), 1258–66.

47. Manthorpe, M., Cornefert-Jensen, F., Hartikka, J., Feigner, J., Rundell, A., Margalith, M., and Dwarki, V. (1993) *Hum Gene Ther* 4(4), 419–31.
48. Rodeck, U., Nishiyama, T., and Mauviel, A. (1999) *Cancer Res* 59(3), 547–50.
49. Igarashi, A., Nashiro, K., Kikuchi, K., Sato, S., Ihn, H., Fujimoto, M., Grotendorst, G. R., and Takehara, K. (1996) *J Invest Dermatol* 106(4), 729–33.
50. Vuorio, T., Kahari, V. M., Black, C., and Vuorio, E. (1991) *J Rheumatol* 18(2), 247–51.
51. Needleman, B. W., Choi, J., Burrows-Mezu, A., and Fontana, J. A. (1990) *Arthritis Rheum* 33(5), 650–6.
52. Pratt, W. B. (1998) *Proc Soc Exp Biol Med* 217(4), 420–34.
53. Yue, L., Karr, T. L., Nathan, D. F., Swift, H., Srinivasan, S., and Lindquist, S. (1999) *Genetics* 151(3), 106579.
54. Rutherford, S. L., and Lindquist, S. (1998) *Nature* 396(6709), 336–42.

What is claimed is:

1. A method of treatment of a fibrogenic disorder in a patient, said method comprising the steps of:
   providing a patient suffering from or believed to be at risk of suffering from a fibrogenic disorder; said fibrogenic disorder characterized by an overexpression or overactivity of TGF-β signaling pathway; and
   administering to said patient an effective amount of a therapeutic composition for treating fibrogenic disorders, said therapeutic composition comprising:
       an inhibitor selected from the group consisting of macbecin, herbimycin, galdanamycin and derivatives and analoge thereof; and
       a pharaceutically acceptable inert carrier vehicle.

2. The method of claim 1, wherein, in said administering step, said composition is administered locally.

3. The method of claim 2, wherein, in said administering step, said composition is administered topically.

4. The method of claim 1, wherein said inhibitor is effective in blocking TGF-β signal transduction.

5. The method of claim 1, wherein said inhibitor interferes with heat shock protein 90 chaperone function.

6. The method of claim 1, wherein said inhibitor is capable of binding to an ATP binding site of heat shock protein 90.

7. The method of claim 1, wherein, in said administering step, said composition is administered at a concentration that is insufficient to detectably affect steroid hormone receptor activity.

8. The method of claim 1, wherein, in said administering step, said composition is administered locally at a concentration of 0.25 µg/kg/day to 2.5 µg/kg/day.

9. The method of claim 1, wherein said fibrogenic disorder is selected from the group consisting of scleroderma, polymyositis, systemic lupus erythematosus, keloid formation, interstitial nephritis liver cirrhosis and pulmonary fibrosis.

10. The method of claim 9, wherein said fibrogenic disorder is selected from the group consisting of scleroderma, keloid formation pulmonary fibrosis and liver cirrhosis.

11. The composition of claim 1, wherein said inhibitor is geldanamycin.

* * * * *

UNITED STATES PATENT AND TRADEMARK OFFICE
CERTIFICATE OF CORRECTION

PATENT NO. : 6,887,853 B2
APPLICATION NO. : 10/312287
DATED : May 3, 2005
INVENTOR(S) : David Strehlow Page 1 of 1

It is certified that error appears in the above-identified patent and that said Letters Patent is hereby corrected as shown below:

Column 8, line 46, "MRNA" should read --mRNA--;

Column 15, claim 1, line 31, "analoge" should read --analogs--; and

Column 16, claim 11, line 28, "composition" should read --method--.

Signed and Sealed this

First Day of August, 2006

JON W. DUDAS
*Director of the United States Patent and Trademark Office*